(12) United States Patent
Watanabe et al.

(10) Patent No.: US 12,258,251 B2
(45) Date of Patent: Mar. 25, 2025

(54) CAP ATTACHING/DETACHING DEVICE, AND SAMPLING DEVICE AND PRE-PROCESSING DEVICE PROVIDED WITH SAME

(71) Applicants: NATIONAL UNIVERSITY CORPORATION KOBE UNIVERSITY, Kobe (JP); SHIMADZU CORPORATION, Kyoto (JP)

(72) Inventors: Tsutomu Watanabe, Kyoto (JP); Akari Oda, Kyoto (JP); Tomohisa Hasunuma, Kobe (JP)

(73) Assignees: NATIONAL UNIVERSITY CORPORATION KOBE UNIVERSITY, Kobe (JP); SHIMADZU CORPORATION, Kyoto (JP)

( * ) Notice: Subject to any disclaimer, the term of this patent is extended or adjusted under 35 U.S.C. 154(b) by 741 days.

(21) Appl. No.: 17/259,619

(22) PCT Filed: Jul. 10, 2019

(86) PCT No.: PCT/JP2019/027324
§ 371 (c)(1),
(2) Date: Jan. 12, 2021

(87) PCT Pub. No.: WO2020/017408
PCT Pub. Date: Jan. 23, 2020

(65) Prior Publication Data
US 2021/0292149 A1    Sep. 23, 2021

(30) Foreign Application Priority Data
Jul. 17, 2018  (JP) ................. 2018-134171

(51) Int. Cl.
*B67B 3/20*    (2006.01)
*C12M 1/00*    (2006.01)

(52) U.S. Cl.
CPC ............... *B67B 3/20* (2013.01); *C12M 23/38* (2013.01)

(58) Field of Classification Search
CPC .......................... B67B 3/20; C12M 23/88
See application file for complete search history.

(56) References Cited

U.S. PATENT DOCUMENTS 2,130,317 A * 9/1938 Clarke ...................... B67B 3/00
53/304
3,589,103 A * 6/1971 Calvillo .................... B67B 7/24
53/381.4

(Continued)

FOREIGN PATENT DOCUMENTS

CN    106495073 A  *  3/2017
JP    04-002485 A     1/1992

(Continued)

OTHER PUBLICATIONS

Communication dated Nov. 30, 2021 from the Japanese Patent Office in Application No. 2020-531263.

(Continued)

*Primary Examiner* — Thomas M Wittenschlaeger
*Assistant Examiner* — David G Shutty
(74) *Attorney, Agent, or Firm* — Sughrue Mion, PLLC (57) ABSTRACT

A cap attaching/detaching device 20 is a device for attaching or detaching a cap 141 in which a screw portion is formed to or from a test tube 14 by rotating the cap 141. A cap grip portion 21 grips the cap 141. A rotation mechanism 22 attaches or detaches the cap 141 to or from the test tube 14 by rotating the cap 141 by rotating the cap grip portion 21. The rotation mechanism 22 has an axial portion 221, and a (Continued)

nut portion 222. The axial portion 221 has an outer peripheral surface on which a screw thread 223 is formed. The nut portion 222 has an inner peripheral surface on which a screw groove 224 to be screwed into the screw thread 223 of the axial portion 221 is formed, and rotatably holds the axial portion 221 in a fixed state. A pitch of the screw thread 223 is the same as a pitch of the screw portion formed in the cap 141.

4 Claims, 5 Drawing Sheets

(56) References Cited

U.S. PATENT DOCUMENTS

| | | | | |
|---|---|---|---|---|
| 4,171,650 | A * | 10/1979 | Cardinal | B67B 7/182 81/3.2 |
| 4,265,071 | A * | 5/1981 | Smith | B67B 7/182 53/492 |
| 4,762,029 | A * | 8/1988 | Chen | B67B 7/182 81/3.2 |
| 5,472,669 | A * | 12/1995 | Miki | B67B 7/182 422/65 |
| 5,533,407 | A * | 7/1996 | Besnier | G01N 35/10 73/864.31 |
| 5,819,508 | A * | 10/1998 | Kraft | B67B 7/182 53/492 |
| 6,257,091 | B1 * | 7/2001 | Cohen | B67B 7/182 81/3.39 |
| 6,871,566 | B2 * | 3/2005 | Niwayama | B67B 7/182 81/3.2 |
| 7,251,921 | B2 * | 8/2007 | Galimberti | B67B 3/2033 53/317 |
| 9,878,890 | B2 * | 1/2018 | Mikhailov | B67B 7/182 |
| 11,061,044 | B2 * | 7/2021 | Yamagata | B67B 7/182 |
| 2004/0005245 | A1 * | 1/2004 | Watson | B65G 47/256 422/65 |
| 2007/0098597 | A1 * | 5/2007 | Brunner | B67B 7/182 422/400 |
| 2012/0252110 | A1 | 10/2012 | Oura et al. | |
| 2012/0318076 | A1 * | 12/2012 | Kappelhoff | G01N 35/0099 73/864.11 |
| 2015/0175289 | A1 * | 6/2015 | Zumbach | B65B 7/2835 53/492 |
| 2018/0066218 | A1 * | 3/2018 | Koike | B25J 18/007 |
| 2019/0119621 | A1 * | 4/2019 | Koike | C12M 23/50 |
| 2021/0292149 | A1 * | 9/2021 | Watanabe | G01N 35/04 |

FOREIGN PATENT DOCUMENTS

| | | |
|---|---|---|
| JP | 2012-200239 A | 10/2012 |
| JP | 2016-064445 A | 4/2016 |
| WO | 2017/069151 A1 | 4/2017 |

OTHER PUBLICATIONS

International Search Report for PCT/JP2019/027324 dated Oct. 8, 2019 [PCT/ISA/210].

Written Opinion for PCT/JP2019/027324 dated Oct. 8, 2019 [PCT/ISA/237].

* cited by examiner

CAP ATTACHING/DETACHING DEVICE, AND SAMPLING DEVICE AND PRE-PROCESSING DEVICE PROVIDED WITH SAME

CROSS REFERENCE TO RELATED APPLICATIONS

This application is a National Stage of International Application No. PCT/JP2019/027324 filed Jul. 10, 2019, claiming priority based on Japanese Patent Application No. 2018-134171 filed Jul. 17, 2018.

TECHNICAL FIELD

The present invention relates to a cap attaching/detaching device for attaching or detaching a cap in which a screw portion is formed, to or from a container by rotating the cap, and a sampling apparatus and a pre-processing apparatus each of which is provided with the cap attaching/detaching device.

BACKGROUND ART

A technology has been known in which an analysis such as metabolome analysis is performed by culturing cells of microorganisms and plants in a culture medium in a culture vessel, collecting cells from the culture medium, performing pre-processing, and then supplying the cells to a liquid chromatograph mass spectrometer. In this kind of technology, a sampling apparatus for sampling a culture medium containing cells and a pre-processing apparatus for performing pre-processing on the cells contained in the sampled culture medium are used. The sampling of the culture medium is performed under an aseptic condition (refer to, for example, Patent Document 1 below).

A cap is attached to the container in which the culture medium is sampled. Generally, the cap is a screw type, and the inside of the container can be sealed with the cap by screwing a screw thread formed on an outer peripheral surface of the container into a screw groove formed on an inner peripheral surface of the cap, and rotating and tightening the cap.

PRIOR ART DOCUMENT

Patent Document

Patent Document 1: Japanese Patent Laid-Open No. 2012-200239

SUMMARY OF THE INVENTION

Problems to be Solved by the Invention

When sampling is performed automatically, it is necessary to automatically attach or detach the cap to or from the container. In this case, it is necessary to simultaneously perform an operation of rotating the cap (rotation operation) and an operation of moving the cap in order to separate the container and the cap from each other or bring the container and the cap closer to each other (movement operation). Therefore, it is conceivable to use a cap attaching/detaching device that is provided with a rotation mechanism for performing the rotation operation and a movement mechanism for performing the movement operation and drives the rotation mechanism and the movement mechanism in synchronization with each other.

However, in a case where separate motors are used for the rotation mechanism and the movement mechanism, the rotation operation and the movement operation are not in synchronization when the torque required for the rotation of the cap fluctuates or the like, and thus there is a risk that the attachment or detachment of the cap cannot be reliably performed. In addition, there are many components for control and drive, and there is a problem that the manufacturing cost is high.

It is also conceivable to connect the rotation mechanism and the movement mechanism using a gear or the like and drive them with one motor. However, even in this case, since the number of components for drive such as a gear is increased, the structure becomes complicated, and a failure is likely to occur.

The above-described problems occur not only at the time of the sampling in which the culture medium is sampled, but also at the time of the pre-processing in which pre-processing is performed on the cells contained in the sampled culture medium. Further, the above-described problems may occur not only in the container for housing the culture medium but also in any container to or from which the cap is rotated to be attached or detached.

The invention has been made in view of the above circumstances, and an object thereof is to provide a cap attaching/detaching device that can reliably perform the attachment or detachment of the cap with a simple configuration, and a sampling apparatus and a pre-processing apparatus which include the same.

Means for Solving the Problems (1) A cap attaching/detaching device according to the invention is a cap attaching/detaching device for attaching or detaching a cap in which a screw portion is formed to or from a container by rotating the cap, and includes a cap grip portion, and a rotation mechanism. The cap grip portion grips the cap. The rotation mechanism attaches or detaches the cap to or from the container by rotating the cap by rotating the cap grip portion.

The rotation mechanism has an axial portion, and a nut portion. The axial portion has an outer peripheral surface on which a screw thread is formed. The nut portion has an inner peripheral surface on which a screw groove to be screwed into the screw thread of the axial portion is formed, and rotatably holds the axial portion in a fixed state. A pitch of the screw thread is the same as a pitch of the screw portion formed in the cap.

According to such a configuration, by rotating the axial portion with respect to the fixed nut portion, the cap grip portion can be moved in the axial direction while being rotated via the axial portion. As a result, the rotation operation and the movement operation of the cap can be simultaneously performed with a simple configuration. In particular, since the pitch of the screw thread formed in the axial portion is the same as the pitch of the screw portion formed in the cap, the rotation operation and the movement operation of the cap can be appropriately performed according to the rotation of the axial portion, and therefore, the attachment or detachment of the cap can be reliably performed.

(2) The cap grip portion may have a displacement portion, and a shaft. The displacement portion is displaced between a state in which the displacement portion grips the cap and a state in which the displacement portion does not grip the cap. The shaft is slid along an axial direction to displace the displacement portion.

According to such a configuration, the displacement portion of the cap grip portion is displaced by sliding the shaft along the axial direction, and thereby the cap can be gripped by the displacement portion. By converting the operation of sliding the shaft into the displacement of the displacement portion in this way, the cap can be gripped with a simple operation.

(3) The axial portion may be formed in a hollow shape. In this case, the shaft may be inserted into an inside of the axial portion.

According to such a configuration, since the shaft that is slid in the axial direction is inserted into the hollow-shaped axial portion, it is possible to prevent the movement of the shaft and the movement of the axial portion from interfering with each other.

(4) The cap attaching/detaching device may further include a movement mechanism. The movement mechanism moves the container attached to the cap gripped by the cap grip portion, by moving the rotation mechanism.

According to such a configuration, not only the cap can be attached or detached, but also the container in a state where the cap is attached can be moved, by using the cap attaching/detaching device. Therefore, it is not necessary to separately provide a device for moving the container, and the configuration becomes simpler.

(5) A sampling apparatus according to the invention is a sampling apparatus for sampling a culture medium containing cells, and includes the cap attaching/detaching device, and a sampling mechanism that samples the culture medium in the container from which the cap is removed by the cap attaching/detaching device.

According to such a configuration, when the culture medium is sampled in the container in the sampling apparatus, the attachment or detachment of the cap can be reliably performed with a simple configuration.

(6) A pre-processing apparatus according to the invention is a pre-processing apparatus for performing pre-processing on cells in a container, and includes the cap attaching/detaching device, and a reagent supply mechanism that supplies a reagent into the container from which the cap is removed by the cap attaching/detaching device.

According to such a configuration, when the reagent is supplied into the container in the pre-processing apparatus, the attachment or detachment of the cap can be reliably performed with a simple configuration.

Effects of the Invention

According to the invention, since the rotation operation and the movement operation of the cap can be appropriately performed with a simple configuration in which the axial portion is simply rotated with respect to the fixed nut portion, the attachment or detachment of the cap can be reliably performed.

MODE FOR CARRYING OUT THE INVENTION

1. Schematic Configuration of Automatic Pre-Processing System

Figure 1:
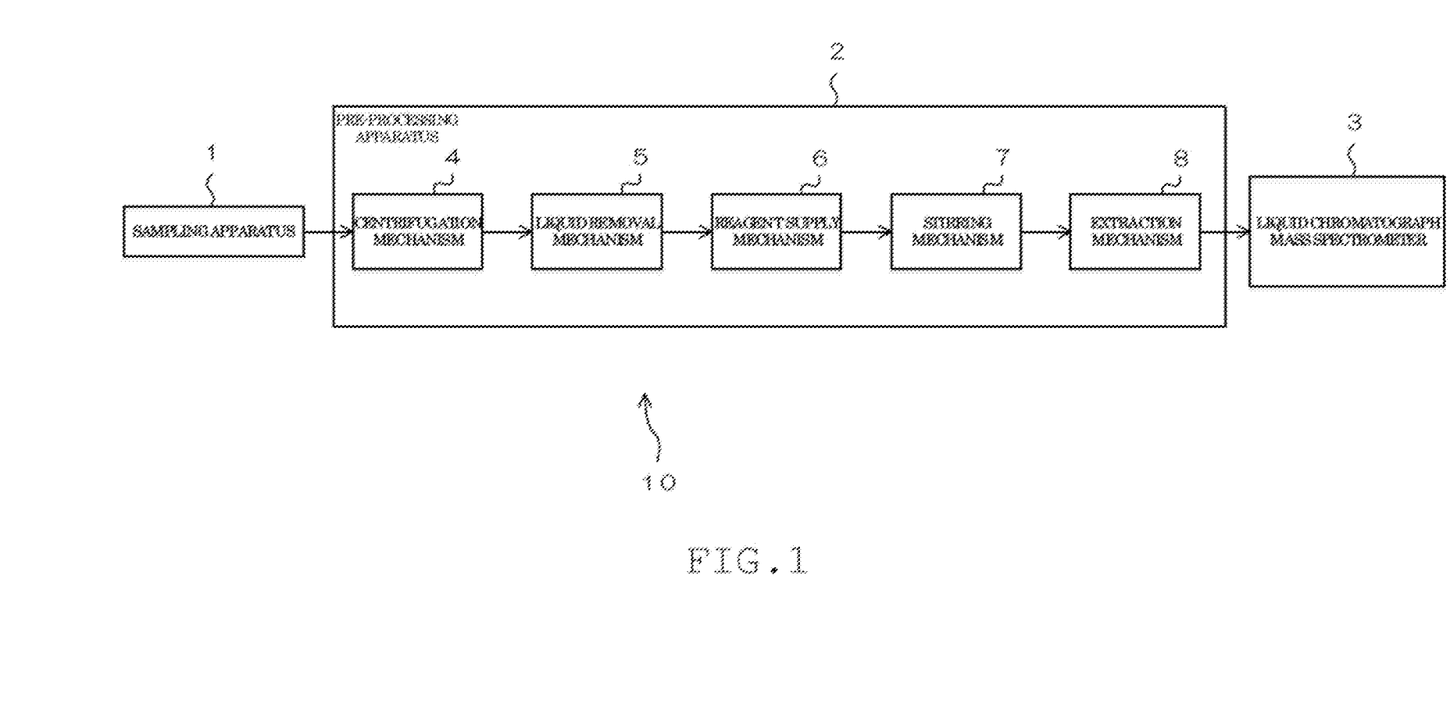
FIG. 1 is a block diagram illustrating a schematic configuration of an automatic pre-processing system including a sampling apparatus and a pre-processing apparatus to which a cap attaching/detaching device according to an embodiment of the invention is applied.

FIG. 1 is a block diagram illustrating a schematic configuration of an automatic pre-processing system 10 including a sampling apparatus 1 and a pre-processing apparatus 2 to which a cap attaching/detaching device according to an embodiment of the invention is applied. The automatic pre-processing system 10 is a device for automatically performing pre-processing on an analysis target. In the present embodiment, the analysis target is, for example, a cultured cell, and more specifically, a bacterial cell.

The automatic pre-processing system 10 includes the sampling apparatus 1 and a pre-processing apparatus 2. The metabolites of the cells are extracted from the cells after the pre-processing is performed by the automatic pre-processing system 10, and are supplied to a liquid chromatograph mass spectrometer 3. The liquid chromatograph mass spectrometer 3 is only an example of an analysis device for analyzing an analysis target, and it is also possible to perform an analysis by using another analysis device.

The sampling apparatus 1 is a apparatus for sampling a liquid from a container (culture container). For example, the cells of microorganisms and plants are cultured in a culture medium in a container called a bioreactor, and the culture medium containing the cells in the bioreactor is sampled by the sampling apparatus 1. In the bioreactor, for example, a stirring member that is rotated by using magnetic force, an oxygen concentration sensor for detecting the concentration of dissolved oxygen, and the like are provided, and the cells are cultured in the sampling apparatus 1 by adjusting the dissolved oxygen concentration while stirring the culture medium in the bioreactor.

The pre-processing apparatus 2 performs pre-processing on the cells contained in the culture medium sampled from the bioreactor. In the sampling apparatus 1, the culture medium containing the cells is housed in a test tube as a container (sampling container). The pre-processing apparatus 2 is provided with a centrifugation mechanism 4, a liquid removal mechanism 5, a reagent supply mechanism 6, a stirring mechanism 7, an extraction mechanism 8, and the like, and by each of these mechanisms, the pre-processing is sequentially performed on the cells contained in the culture medium in the test tube.

The centrifugation mechanism 4 centrifuges the test tube in which the culture medium containing the cells is housed. As a result, centrifugal force is applied to the culture medium in the test tube, and the cells (solid) and the liquid other than the cells are separated. Then, the liquid other than the cells centrifuged in the test tube by the centrifugation mechanism 4 is removed by using the liquid removal mechanism 5, and thereby the cells are collected.

The reagent is supplied by the reagent supply mechanism 6, to the test tube after the liquid is removed by the liquid removal mechanism 5. As a result, the reagent is mixed with the cells in the test tube, and a mixed solution is generated. Then, the mixed solution generated by the reagent supply mechanism 6 is stirred by the stirring mechanism 7.

The reagent used in the present embodiment is a reagent for extracting metabolites in the cells, and a suspension in which the metabolites are extracted from the cells is obtained by stirring the mixed solution in which the reagent is mixed with the cells. A part of the suspension obtained in this manner is extracted as an extraction liquid by the extraction mechanism 8, and is supplied to the liquid chromatograph mass spectrometer 3.

2. Specific Configuration of Cap Attaching/Detaching Device

Figure 2:
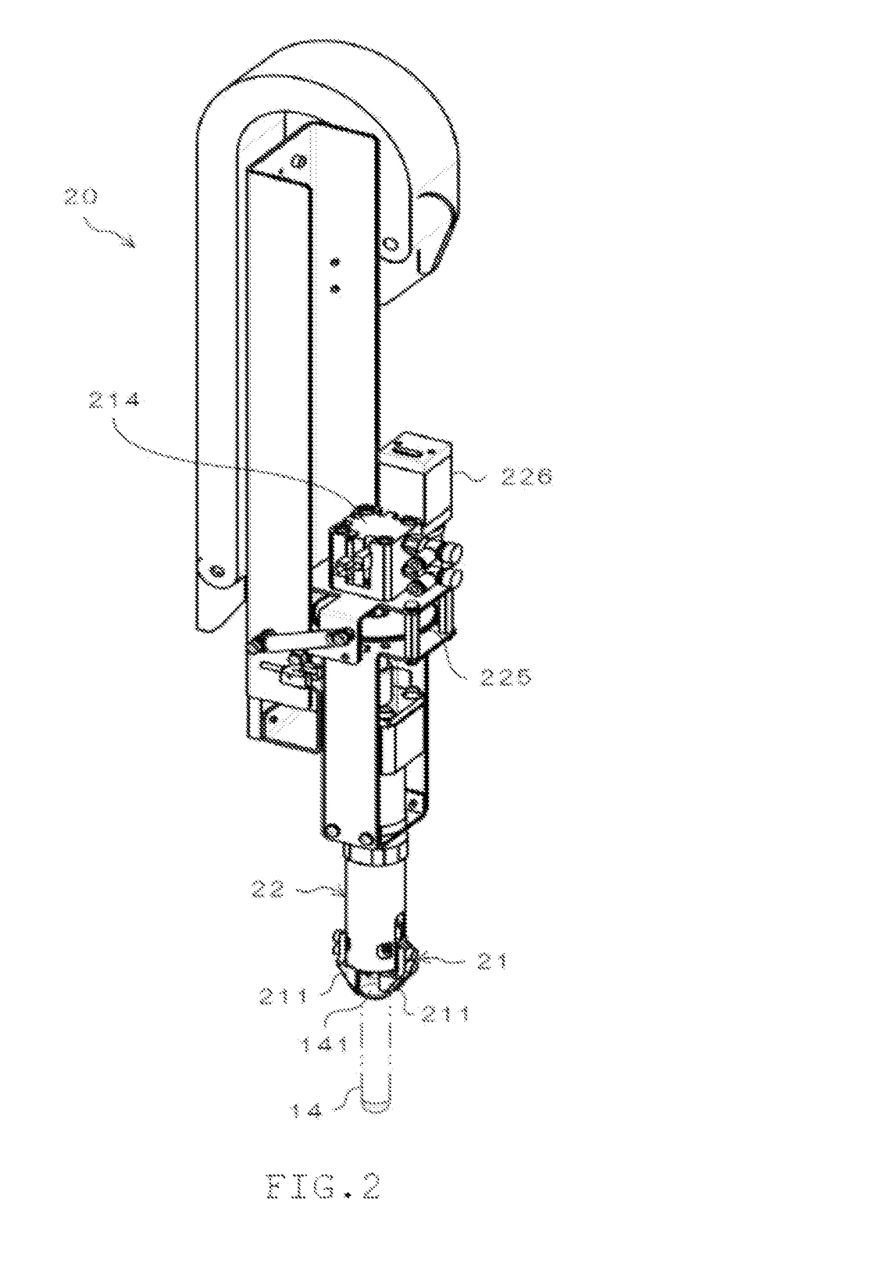
FIG. 2 is a perspective view of the cap attaching/detaching device.
Figure 3:
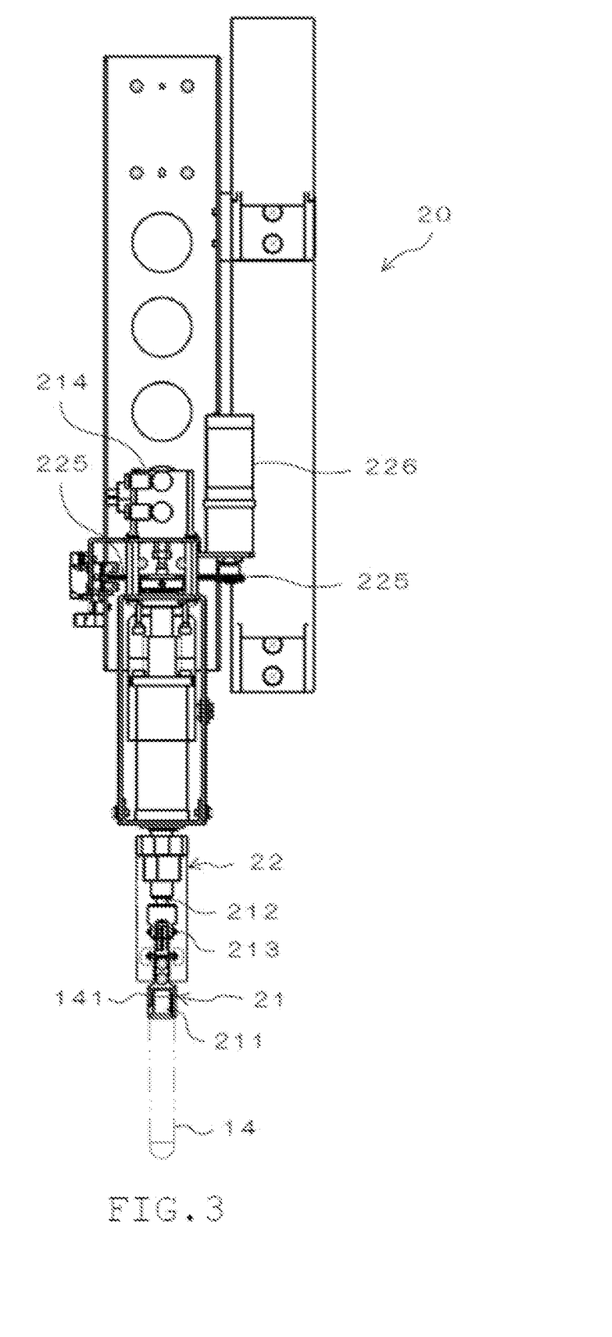
FIG. 3 is a front view of the cap attaching/detaching device.
Figure 4:
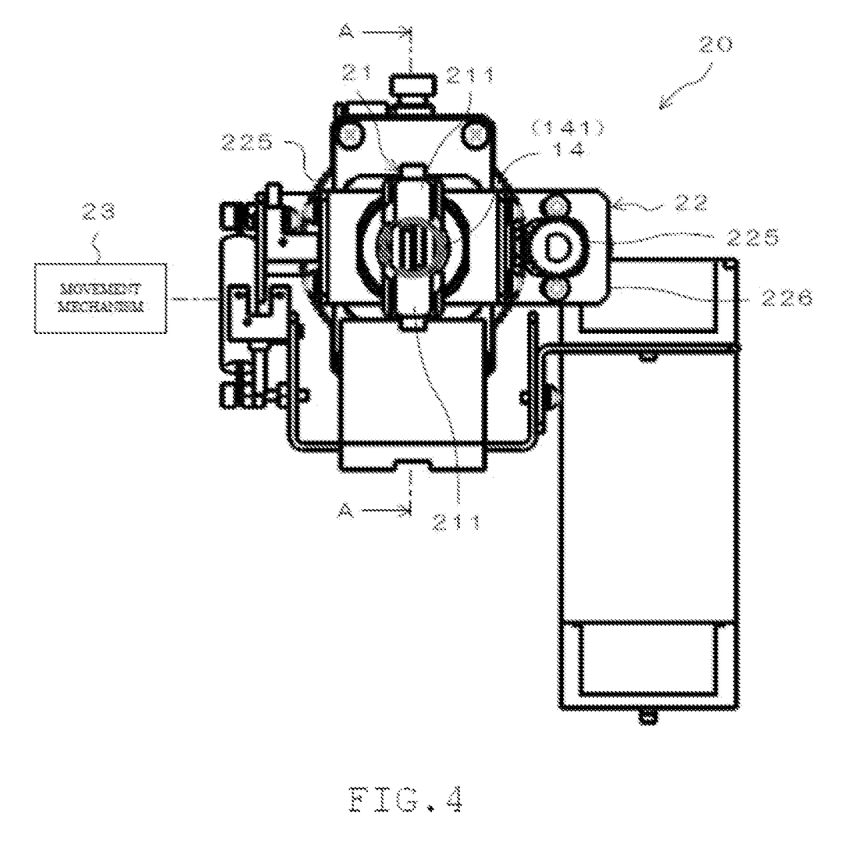
FIG. 4 is a bottom view of the cap attaching/detaching device.
Figure 5:
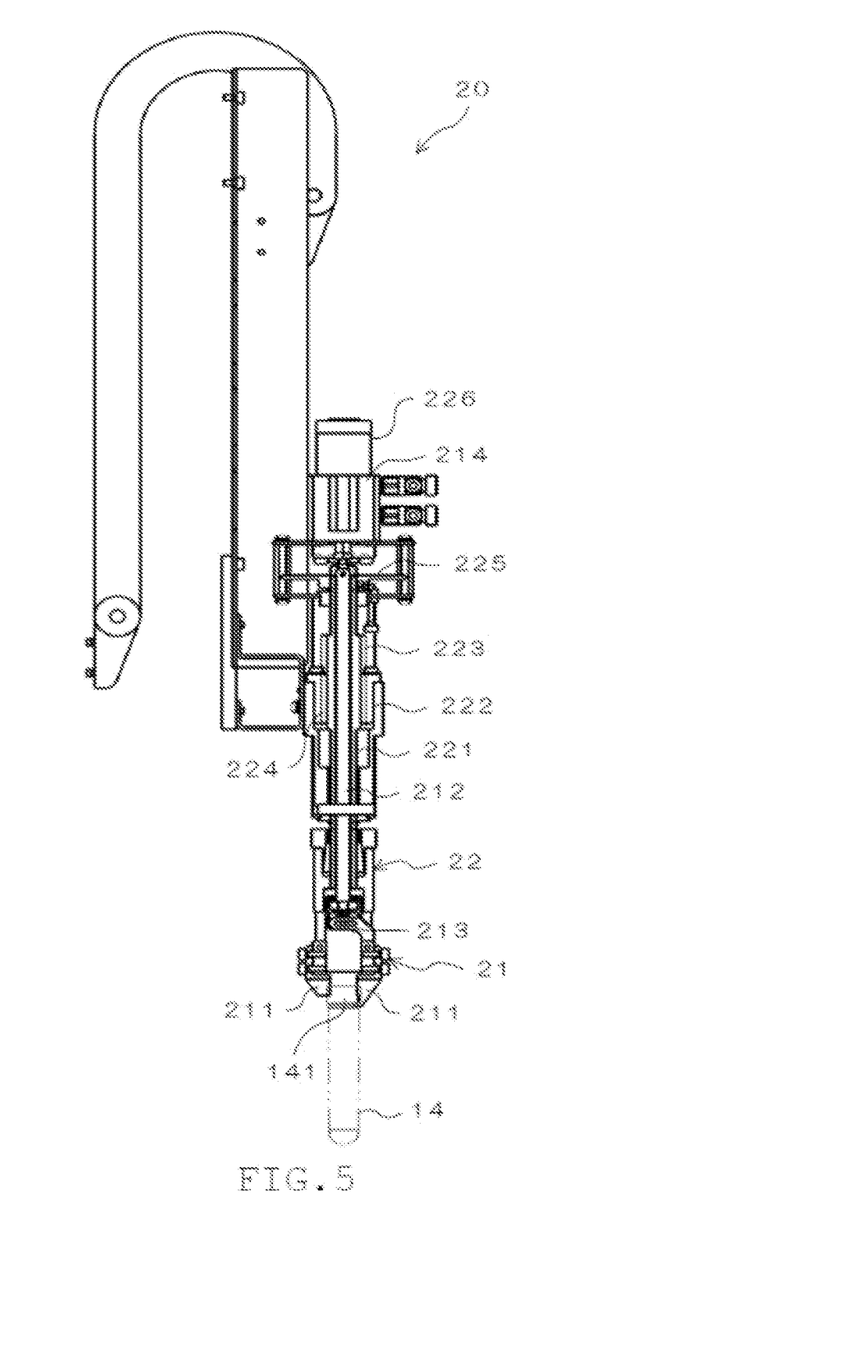
FIG. 5 is a sectional view taken along line A-A of the cap attaching/detaching device of FIG. 4.

FIG. 2 is a perspective view of a cap attaching/detaching device 20. FIG. 3 is a front view of the cap attaching/detaching device 20. FIG. 4 is a bottom view of the cap attaching/detaching device 20. FIG. 5 is a sectional view taken along line A-A of the cap attaching/detaching device 20 of FIG. 4.

In the present embodiment, a cap 141 is attached or detached by the cap attaching/detaching device 20 to or from a test tube 14 in which the culture medium is housed in the sampling apparatus 1. The cap 141 is a screw type, and the inside of the test tube 14 can be sealed by screwing a screw thread formed on an outer peripheral surface of the test tube 14 into a screw groove (screw portion) formed on an inner peripheral surface of the cap 141, and rotating and tightening the cap 141.

The cap 141 is attached to the test tube 14 in a state in which the inside is empty, and the test tube 14 is set in the sampling apparatus 1. A plurality of test tubes 14 can be set in the sampling apparatus 1, and the respective test tubes 14 are sequentially transferred and used. When the culture medium is sampled in each test tube 14 in the sampling apparatus 1, the cap 141 is removed from the test tube 14 by the cap attaching/detaching device 20, the culture medium is sampled in the test tube 14, and then the cap 141 is attached to the test tube 14 again.

The cap attaching/detaching device 20 can be applied not only to the sampling apparatus 1 but also to the pre-processing apparatus 2. That is, in a case where the test tube 14 in which the culture medium is housed is transferred from the sampling apparatus 1 to the pre-processing apparatus 2, the cap attaching/detaching device 20 may be used when the cap 141 is attached or detached to or from the test tube 14. In this case, the cap 141 is removed from the test tube 14 by the cap attaching/detaching device 20 after centrifugation by the centrifugation mechanism 4, the liquid other than the cells is removed from the test tube 14 by the liquid removal mechanism 5, the reagent is supplied into the test tube 14 by the reagent supply mechanism 6, and then the cap 141 is attached to the test tube 14 by the cap attaching/detaching device 20 again.

The cap attaching/detaching device 20 includes a cap grip portion 21 that grips the cap 141, and a rotation mechanism 22 that rotates the cap grip portion 21. When the cap grip portion 21 is rotated by the rotation mechanism 22 in a state where the cap 141 is gripped by the cap grip portion 21, the cap 141 can be rotated to be attached or detached to or from the test tube 14.

The cap grip portion 21 includes one pair of displacement portions 211 and a shaft 212 for displacing the one pair of displacement portions 211. The one pair of displacement portions 211 is claw-shaped members arranged to face each other, and the cap 141 can be gripped by being interposed between the one pair of displacement portions 211.

The one pair of displacement portions 211 is supported to be swingable around a support shaft 213. When the one pair of displacement portions 211 swings around the support shaft 213, the one pair of displacement portions 211 can be displaced between a state in which the tip end portions are close to each other and a state in which the tip end portions are separated from each other. When gripping the cap 141, the tip end portions of the one pair of displacement portions 211 are in a state of being close to each other, and the cap 141 can be gripped by the tip end portions. From this state, when the one pair of displacement portions 211 swings around the support shaft 213 so that the tip end portions thereof are separated more than the outer diameter of the cap 141, the one pair of displacement portions 211 is in a state of not gripping the cap 141.

In a state where the cap 141 is gripped by the one pair of displacement portions 211, the test tube 14 to which the cap 141 is attached is held in a state where the axial direction thereof extends in a vertical direction. In this state, the test tube 14 is in a state where the test tube 14 cannot rotate about the axis line. That is, since the outer peripheral surface of the test tube 14 is fixed, even in a case where the cap 141 is rotated, the test tube 14 is not rotated. Specifically, the outer peripheral surface of the test tube 14 may be fixed at an installation position where the test tube 14 is installed, or the cap attaching/detaching device 20 may include a fixing mechanism for fixing the outer peripheral surface of the test tube 14.

The shaft 212 extends coaxially (vertical direction) with the test tube 14 gripped by the one pair of displacement portions 211. The shaft 212 is held to be slidable along its axial direction, and the one pair of displacement portions 211 can be displaced by sliding the shaft 212. Specifically, when the shaft 212 is slid downward, the tip end portions of the one pair of displacement portions 211 are separated, and when the shaft 212 is slid upward, the tip end portions of the one pair of displacement portions 211 are brought closer to each other. The shaft 212 can be slid by, for example, a drive source such as a cylinder 214 provided in the cap grip portion 21.

The rotation mechanism 22 includes a hollow-shaped axial portion 221 and a nut portion 222 that rotatably holds the axial portion 221. When the axial portion 221 is rotated, the one pair of displacement portions 211 of the cap grip portion 21 can be rotated. The axial portion 221 extends coaxially (vertical direction) with the shaft 212 of the cap grip portion 21, and the shaft 212 is inserted into the inside of the axial portion 221. The inner diameter of the axial portion 221 is larger than the outer diameter of the shaft 212. Therefore, even in a case where the axial portion 221 is rotated, no external force is applied to the shaft 212, and the shaft 212 is not rotated.

A screw thread 223 is formed on the outer peripheral surface of the axial portion 221. Further, a screw groove 224 to be screwed into the screw thread 223 of the axial portion 221 is formed on the inner peripheral surface of the nut portion 222. The nut portion 222 is fixed at a predetermined position in the cap attaching/detaching device 20, and the axial portion 221 is held to be rotatable with respect to the nut portion 222 in a fixed state, by screwing the axial portion 221 into the nut portion 222. Therefore, when the axial portion 221 is rotated, the axial portion 221 is moved in the axial direction (vertical direction) while being rotated with respect to the nut portion 222 in the fixed state.

A motor 226 provided in the rotation mechanism 22 is connected to the axial portion 221 via a plurality of gears 225. As a result, when the motor 226 is rotated, the axial portion 221 is rotated via the plurality of gears 225, and accordingly, the one pair of displacement portions 211 of the cap grip portion 21 can be moved in the axial direction while being rotated.

In the present embodiment, the pitch of the screw thread 223 formed on the outer peripheral surface of the axial portion 221 is the same as the pitch of the screw groove formed on the inner peripheral surface of the cap 141. Therefore, a movement amount of the axial portion 221 with respect to the nut portion 222 per rotation and a movement amount of the cap 141 with respect to the test tube 14 per rotation are the same.

As conceptually illustrated in FIG. 4, the cap grip portion 21 and the rotation mechanism 22 can be integrally moved by a movement mechanism 23. The movement mechanism 23 includes, for example, a motor and a plurality of gears (neither illustrated), and can move the test tube 14 attached to the cap 141 gripped by the cap grip portion 21, by moving the rotation mechanism 22 in the vertical direction and a horizontal direction.

3. Effects (1) In the present embodiment, by rotating the axial portion 221 with respect to the fixed nut portion 222, the cap grip portion 21 can be moved in the axial direction (vertical direction) while being rotated via the axial portion 221. As a result, the rotation operation and the movement operation of the cap 141 can be simultaneously performed with a simple configuration. In particular, since the pitch of the screw thread 223 formed in the axial portion 221 is the same as the pitch of the screw portion formed in the cap 141, the rotation operation and the movement operation of the cap 141 can be appropriately performed according to the rotation of the axial portion 221, and therefore, the attachment or detachment of the cap 141 can be reliably performed.

(2) In the present embodiment, the one pair of displacement portions 211 of the cap grip portion 21 is displaced by sliding the shaft 212 along the axial direction (vertical direction), and thereby the cap 141 can be gripped by the displacement portions 211. By converting the operation of sliding the shaft 212 into the displacement of the one pair of displacement portions 211 in this way, the cap 141 can be gripped with a simple operation.

(3) In the present embodiment, the shaft 212 that is slid in the axial direction (vertical direction) is inserted into the hollow-shaped axial portion 221. Therefore, it is possible to prevent the operation of the shaft 212 and the operation of the axial portion 221 from interfering with each other.

(4) In the present embodiment, by moving the rotation mechanism 22 by the movement mechanism 23, not only the cap 141 can be attached or detached, but also the test tube 14 in a state where the cap 141 is attached can be moved, by using the cap attaching/detaching device 20. Therefore, it is not necessary to separately provide a device for moving the test tube 14, and the configuration becomes simpler.

4. Modification Example

In the above embodiment, the case where the displacement portion that grips the cap 141 is composed of one pair of claw-shaped displacement portions 211 has been described. However, without being limited to such a configuration, the displacement portion provided in the cap grip portion 21 may have any other configuration as long as the displacement portion can be displaced between a state where the displacement portion grips the cap 141 and a state where the displacement portion does not grip the cap 141. Further, without being limited to a configuration in which the cap 141 is gripped by the displacement portion, the cap grip portion 21 may adopt any other configuration as long as the cap 141 can be gripped.

Without being limited to a configuration of being arranged to extend in the vertical direction, the axial portion 221 may be arranged to extend in a direction intersecting the vertical direction. In this case, the test tube 14 is also arranged to extend in the direction intersecting the vertical direction (coaxially with the axial portion 221).

Without being limited to a configuration in which the screw groove formed on the inner peripheral surface of the cap 141 is screwed into the screw thread formed on the outer peripheral surface of the test tube 14, the cap 141 to be attached or detached to or from the test tube 14 may be configured such that the screw thread formed on the outer peripheral surface of the cap 141 is screwed into the screw groove formed on the inner peripheral surface of the test tube 14.

The cap attaching/detaching device 20 according to the invention can be applied to any other apparatus without being limited to the sampling apparatus 1 and the pre-processing apparatus 2. That is, the cap attaching/detaching device 20 can be used when attaching or detaching the cap to or from any other container, without being limited to the test tube 14.

DESCRIPTION OF REFERENCE SIGNS 1 sampling apparatus
2 pre-processing apparatus
3 liquid chromatograph mass spectrometer
4 centrifugation mechanism
5 liquid removal mechanism
6 reagent supply mechanism
7 stirring mechanism
8 extraction mechanism
10 automatic pre-processing system
14 test tube
20 cap attaching/detaching device
21 cap grip portion
22 rotation mechanism
23 movement mechanism
141 cap
211 displacement portion
212 shaft
213 support shaft
214 cylinder
221 axial portion
222 nut portion
223 screw thread
224 screw groove
225 gear
226 motor

The invention claimed is:

1. A cap attaching/detaching device for attaching or detaching a cap in which a screw portion is formed to or from a container by rotating the cap, the cap attaching/detaching device comprising:
 a cap grip portion that grips the cap;

a rotation mechanism that attaches or detaches the cap to or from the container by rotating the cap by rotating the cap grip portion; and a movement actuator for moving the container attached to the cap gripped by the cap grip portion, by moving the rotation mechanism;

wherein the rotation mechanism has
an axial portion that has an outer peripheral surface on which a screw thread is formed, and
a nut portion that has an inner peripheral surface on which a screw groove to be screwed into the screw thread of the axial portion is formed, and rotatably holds the axial portion in a fixed state, wherein a pitch of the screw thread is configured to be the same as a pitch of the screw portion formed in the cap, wherein the cap grip portion has
a displacement claw that is configured to displace between a first state in which the displacement claw grips the cap and a second state in which the displacement claw does not grip the cap, and
a shaft that is slid along an axial direction to displace the displacement claw; and wherein the cap attaching/detaching device further comprises a motor that is connected to the rotation mechanism, and the cap grip portion is moved in the axial direction while being rotated as the axial portion is rotated by the motor, the cap grip portion and the rotation mechanism are integrally moved by the movement actuator, the movement actuator moves the container attached to the cap gripped by the cap grip portion, by moving the rotation mechanism in a vertical direction and a horizontal direction;

the motor is provided in the rotation mechanism, and
the motor is moved by the movement actuator together with the container attached to the cap gripped by the cap grip portion.

2. The cap attaching/detaching device according to claim 1, wherein
the axial portion is formed in a hollow shape, and
the shaft is inserted into an inside of the axial portion.

3. A sampling system for sampling a culture medium containing cells, the sampling system comprising:
a sampling apparatus configured to sample the culture medium containing the cells; and
a cap attaching/detaching device for attaching or detaching a cap in which a screw portion is formed to or from a container by rotating the cap, the cap attaching/detaching device comprising:
a cap grip portion that grips the cap; and
a rotation mechanism that attaches or detaches the cap to or from the container by rotating the cap by rotating the cap grip portion, and
a movement actuator for moving the container attached to the cap gripped by the cap grip portion, by moving the rotation mechanism;

wherein the rotation mechanism has
an axial portion that has an outer peripheral surface on which a screw thread is formed, and
a nut portion that has an inner peripheral surface on which a screw groove to be screwed into the screw thread of the axial portion is formed, and rotatably holds the axial portion in a fixed state, wherein a pitch of the screw thread is configured to be the same as a pitch of the screw portion formed in the cap, wherein the cap grip portion has
a displacement claw that is configured to displace between a first state in which the displacement claw grips the cap and a second state in which the displacement claw does not grip the cap, and
a shaft that is slid along an axial direction to displace the displacement claw, and wherein the sampling apparatus is configured to sample the culture medium in the container after the cap has been removed by the cap attaching/detaching device, and wherein the cap attaching/detaching device further comprises a motor that is connected to the rotation mechanism, and the cap grip portion is moved in the axial direction while being rotated as the axial portion is rotated by the motor, the cap grip portion and the rotation mechanism are integrally moved by the movement actuator, and the movement actuator moves the container attached to the cap gripped by the cap grip portion, by moving the rotation mechanism in a vertical direction and a horizontal direction, the motor is provided in the rotation mechanism, and
the motor is moved by the movement actuator together with the container attached to the cap gripped by the cap grip portion.

4. A pre-processing apparatus for performing pre-processing on cells in a container, the pre-processing apparatus comprising:
a reagent supply dispenser; and
a cap attaching/detaching device for attaching or detaching a cap in which a screw portion is formed to or from a container by rotating the cap, the cap attaching/detaching device comprising:
a cap grip portion that grips the cap; and
a rotation mechanism that attaches or detaches the cap to or from the container by rotating the cap by rotating the cap grip portion, and
a movement actuator for moving the container attached to the cap gripped by the cap grip portion, by moving the rotation mechanism;

wherein the rotation mechanism has
an axial portion that has an outer peripheral surface on which a screw thread is formed, and
a nut portion that has an inner peripheral surface on which a screw groove to be screwed into the screw thread of the axial portion is formed, and rotatably holds the axial portion in a fixed state, wherein a pitch of the screw thread is configured to be the same as a pitch of the screw portion formed in the cap, wherein the cap grip portion has
a displacement claw that is configured to displace between a first state in which the displacement claw grips the cap and a second state in which the displacement claw does not grip the cap, and
a shaft that is slid along an axial direction to displace the displacement claw, and wherein the reagent supply dispenser is configured to supply a reagent into the container after the cap has been removed by the cap attaching/detaching device, and wherein the cap attaching/detaching device further comprises a motor that is connected to the rotation mechanism, and the cap grip portion is moved in the axial direction while being rotated as the axial portion is rotated by the motor, the cap grip portion and the rotation mechanism are integrally moved by the movement actuator, and the movement actuator moves the container attached to the cap gripped by the cap grip portion, by moving the rotation mechanism in a vertical direction and a horizontal direction, the motor is provided in the rotation mechanism, and the motor is moved by the movement actuator together with the container attached to the cap gripped by the cap grip portion.

* * * * *